United States Patent
Zadeh et al.

(10) Patent No.: US 10,809,513 B2
(45) Date of Patent: Oct. 20, 2020

(54) FUNCTIONALIZED OPTICAL LENS AND METHOD OF MANUFACTURING

(71) Applicant: United Arab Emirates University, Al Ain (AE)

(72) Inventors: Ebrahim Ghafar Zadeh, Toronto (CA); Falah Awwad, Al Ain (AE)

(73) Assignee: UNITED ARAB EMIRATES UNIVERSITY, Al Ain (AE)

(*) Notice: Subject to any disclaimer, the term of this patent is extended or adjusted under 35 U.S.C. 154(b) by 0 days.

(21) Appl. No.: 15/615,138

(22) Filed: Jun. 6, 2017

(65) Prior Publication Data
US 2018/0348498 A1 Dec. 6, 2018

(51) Int. Cl.
| | |
|---|---|
| *G02B 21/36* | (2006.01) |
| *G02B 21/32* | (2006.01) |
| *G02B 6/32* | (2006.01) |
| *G02B 21/02* | (2006.01) |
| *G02B 21/00* | (2006.01) |
| *G02B 3/00* | (2006.01) |
| *C12N 13/00* | (2006.01) |

(52) U.S. Cl.
CPC .......... *G02B 21/361* (2013.01); *C12N 13/00* (2013.01); *G02B 3/0012* (2013.01); *G02B 6/325* (2013.01); *G02B 21/0004* (2013.01); *G02B 21/02* (2013.01); *G02B 21/32* (2013.01); *G02B 21/362* (2013.01); *G02B 21/368* (2013.01)

(58) Field of Classification Search
CPC .... C12N 15/87; C12N 15/8206; C12M 35/02; C12M 35/00; G02B 21/361; G02B 21/0004; G02B 21/02; G02B 21/362; G02B 21/368; G02B 3/0012; G02B 6/325

USPC .................... 359/656; 435/461, 173.6, 285.2
See application file for complete search history.

(56) References Cited

U.S. PATENT DOCUMENTS

| | | | |
|---|---|---|---|
| 2005/0149184 A1* | 7/2005 | Bogaert | A61F 2/1602 623/6.14 |
| 2008/0049572 A1* | 2/2008 | Sasabe | G11B 7/1275 369/44.32 |
| 2013/0030352 A1* | 1/2013 | Seymour | A61N 5/0622 604/20 |

(Continued)

FOREIGN PATENT DOCUMENTS

| | | | | |
|---|---|---|---|---|
| JP | 61-065433 | * | 4/1986 | H01L 21/30 |

OTHER PUBLICATIONS

Li Y, Wu M, Zhao D, et al. Electroporation on microchips: the harmful effects of pH changes and scaling down. Scientific Reports. 2015;5:17817. doi:10.1038/srep17817.*

(Continued)

*Primary Examiner* — Travis S Fissel
(74) *Attorney, Agent, or Firm* — Hayes Soloway P.C.

(57) ABSTRACT

There is provided an optical lens having an optically transparent surface coated with transducers adapted to stimulate a stimulus signal in a sample, where the optical lens is adapted to enable an optical communication between an optical source from one side of the optically transparent surface and the transducers and the sample from another side of the optically transparent surface for enabling the optical source to conduct optical operations capturing both the transducers and the sample simultaneously during a stimulation process. There is also provided a method of manufacturing the optical lens.

17 Claims, 7 Drawing Sheets

(56) References Cited

U.S. PATENT DOCUMENTS

2016/0124195 A1* 5/2016 Chern ................ G02B 13/0055
359/355
2016/0266362 A1* 9/2016 Kapanidis .......... G02B 21/0008

OTHER PUBLICATIONS

The construction of an individually addressable cell array for selective patterning and electroporation, Lab Chip, 2011, 11, 2417, Xu et al. (Year: 2011).*

* cited by examiner

FUNCTIONALIZED OPTICAL LENS AND METHOD OF MANUFACTURING

FIELD OF THE INVENTION

The present invention relates to an optical lens used for viewing biological samples, and more particularly to a functionalised optical lens having transducers thereon and method of manufacturing said functionalised optical lens.

BACKGROUND OF INVENTION

Electroporation process is a molecular biology technique in which an electrical field is applied to cells in order to increase the permeability of the cell membrane, allowing chemical compounds, drugs, or Deoxyribo Nucleic Acid (known as DNA) to be introduced into the cell. Electroporation (also known as electropermeabilization) is a physical method to introduce molecules into the cell in vivo and in vitro assays. It consists of generating nano-scale pores induced on the cell membrane by applying controlled electric fields. In molecular biology, the process of electroporation is often used to transform bacteria, yeast or plant protoplasts by introducing new coding DNA. Electroporation is also highly efficient for the introduction of foreign genes into tissue culture cells. The process is especially useful for various applications such as, tumor treatment, gene therapy and cell-based therapy, among others.

Conventional electroporation techniques consist mainly of first isolating the cells from their natural medium and then immersing the cell in a conductive medium and exposing the cell to an electrical field. While the electroporation of a single cell allows studying new methods of cell manipulation, which can be advantageous to improve responses for specific cells according to their morphology and to the configuration of the electric field applied, the efficiency of this process is low, since most single cells die when removed from their natural environment. In addition to this high cell mortality and low efficiency, current methods require large amount of sample reagents and longer times to repeat the test for finding the optimum conditions. Furthermore, conventional electroporation methods cannot be easily integrated with real-time monitoring techniques for direct visualization of what is occurring with the cells/samples, which is very useful for studying the uptake mechanism of the chemicals or drug probes within the cells.

Electroporation process is a non-invasive method only if the electrical fields present around the cells do not exceed a threshold electrical field. However, the electrical field threshold is very difficult to control since said electrical field depends on a multitude of factors. Such factors include the geometries (the distance between the electrodes, the width, length and thickness of each electrode) and material properties (conductivity and surface roughness of electrodes), the electrical conditions (the amplitude, pulse rate and pulse duration of the electrical voltage applied) Also the electrical fields depend on the biochemical conditions (the electrical properties of culture medium, the type of living cells and the transfection molecules used).

Electroporation process may require other types of devices that are used for sensing the biochemical microenvironment conditions (e.g. pH, conductivity, dielectric properties) and for electromagnetic, electrophoresis and di-electrophoresis manipulation purposes using electrodes or coils implemented on the surface of optical lens.

Due to the current drawbacks, including low efficiency, high cell mortality, and other difficulties highlighted above, there remains a need for a system which has the capability of optimizing the electroporation process (including optimization of the electrical and biochemical conditions) for increasing the efficiency of transfection and ensuring high cell viability. Additionally there remains a need for a system and method that has the capability to stimulate these conditions and to monitor the activity of the cells during this process in real time through direct visualization of a stimulation process.

SUMMARY OF THE INVENTION

As a first aspect of the invention, there is provided an optical lens having an optically transparent surface coated with transducers which are adapted to stimulate a stimulus signal in a sample. The optical lens is adapted to enable an optical communication between an optical source from one side of the optically transparent surface and the transducers and the sample from another side of the surface, for enabling the optical source to conduct optical operations capturing both the transducers and the sample simultaneously during a stimulation process.

In one embodiment, the optical lens is a microscope objective lens and the optical source is a microscope.

The optical lens can be a lens cap adapted to be mechanically coupled to a microscope objective, and the optical source can be a microscope.

Preferably, the sample and the transducers have a microscopic scale, and the stimulation and optical operations are conducted at a microscopic scale.

Preferably, the optical operations comprise observing, monitoring or recording images of the transducers and the sample during the stimulation process.

Preferably, the optically transparent surface is comprised of glass, silicon or a polymer.

In one embodiment, the transducers comprise a microelectrode array and the stimulus signal is an electrical signal.

Preferably, the sample comprises one or more living cells for conducting electroporation through the stimulation of the electrical signal in the one or more living cells.

In another embodiment, the transducers can comprise magnetic coils and the stimulus signal can be a magnetic field.

Preferably, the optical lens further comprises a microfluidic structure adapted to inject fluid inside the sample.

Preferably, the transducers are coated on the optically transparent surface with spaces formed between them through which the fluid is directed from the microfluidic structure to the sample.

Preferably, the transducers are microelectrodes, the stimulus signal is an electrical field, the sample comprises one or more living cells, the fluid is a drug for injection inside the one or more living cells during the stimulation process, and the stimulation process is an electroporation of the one or more living cells using the electrical field.

As a further aspect of the invention, there is provided a system comprising:
an optical lens having an optically transparent surface coated with transducers adapted to stimulate a stimulus signal in a sample, where the optical lens is adapted to enable an optical communication between an optical source from one side of the optically transparent surface and the transducers and the sample from another side of the surface, for enabling the optical source to conduct optical operations capturing both the transducers and the sample simultaneously during a stimulation process.

a stimulus generator adapted to be connected to the transducers for generating and transmitting the stimulus signal to the transducers;

an operating device adapted to be connected to the stimulus generator for controlling the stimulus generator.

Preferably:

the transducers comprise an array of microelectrodes and the stimulus signal is an electrical signal having signal characteristics;

the stimulus generator is a programmable electrical pulse generator; and the operating device controls the pulse generator by specifying the signal characteristics of the electrical stimulus signal.

Preferably, the operating device is adapted to be connected to the optical source for receiving and processing images captured through the optical operations.

Preferably, the optical lens is a microscope objective lens or a lens cap adapted to be mechanically coupled to a microscope objective lens, and the optical source is a microscope.

Preferably, the operating device is adapted to be connected to an adjustment mechanism of the microscope for position adjustment of the optical lens with respect to the sample.

Preferably, the position adjustment is three dimensional and in the scale of centimetres to micrometres.

Preferably, the sample comprises one or more living cells for electroporation through the stimulation of the electrical signal in the one or more living cells.

As a further aspect of the invention, there is provided a method of manufacturing a stimulation device for use with an optical source, the method comprising coating transducers on an optically transparent surface of an optical lens, the transducers being adapted to stimulate a stimulus signal in a sample. The optical lens is adapted to enable an optical communication between the optical source from one side of the surface and the transducers and the sample from another side of the surface for enabling the optical source to conduct optical operations capturing both the transducers and the sample simultaneously during a stimulation process.

Preferably, the transducers are microelectrodes, the optical source is a microscope, the optical lens is a microscope objective lens or a cap adapted to be coupled to a microscope objective lens.

Preferably, the method further comprises integrating a microfluidics structure above the microelectrodes for directing a fluid inside the sample.

DETAILED DESCRIPTION OF THE INVENTION

Figure 1:
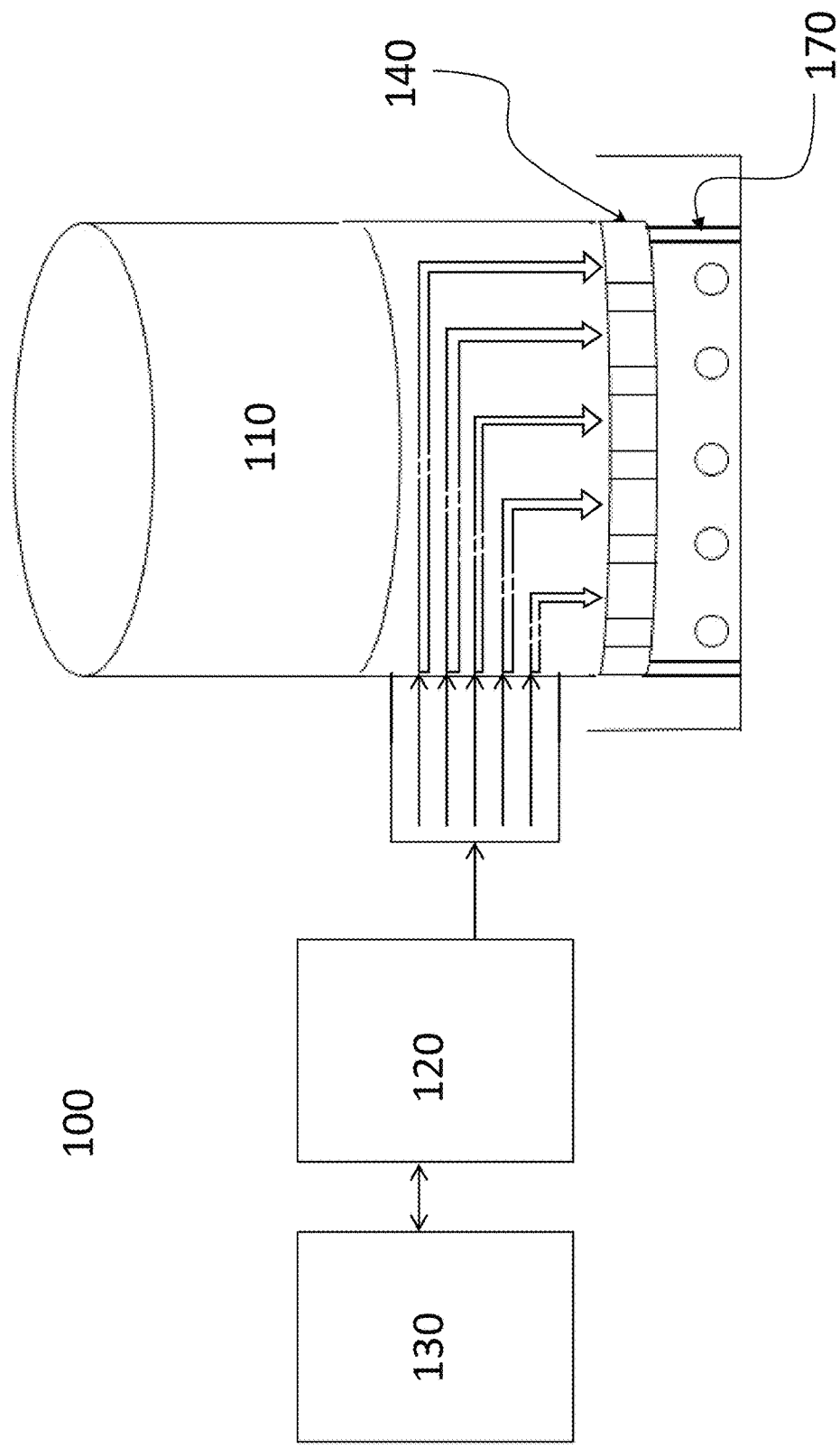
FIG. 1 illustrates a system according to an embodiment of the present invention.
Figure 2:
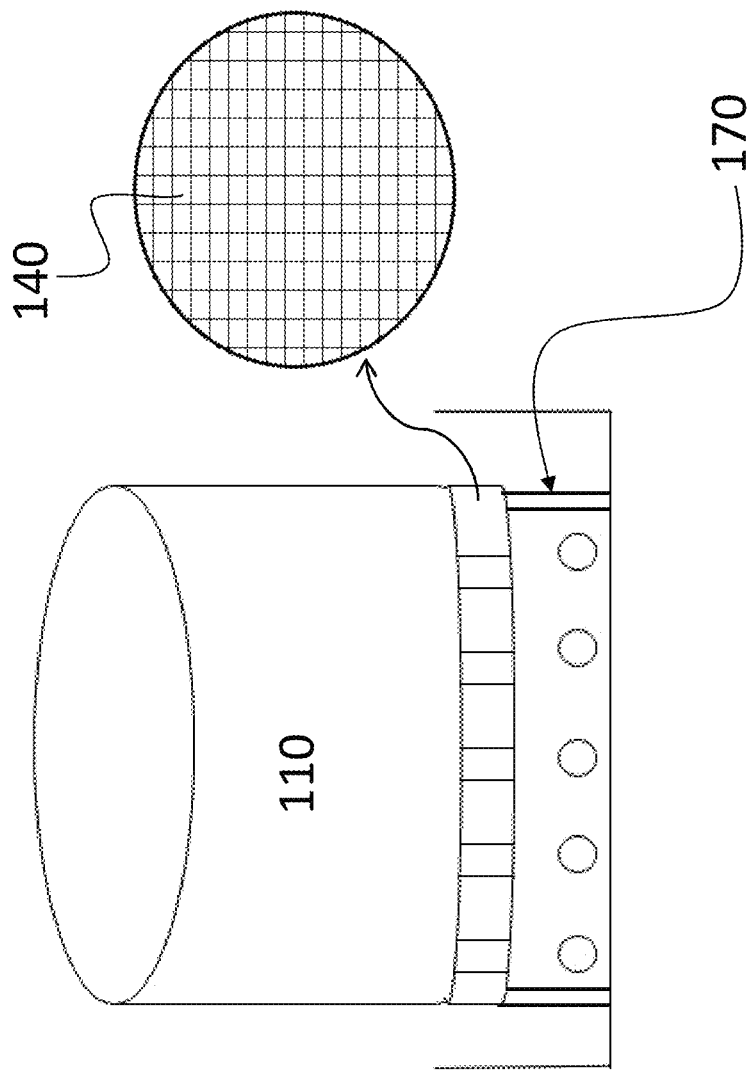
FIG. 2 illustrates functionalized optical lens or optical lens cap in accordance with an embodiment of the present invention.

Illustrated in FIGS. 1 and 2, there is provided a system 100 for stimulating a sample 170 at a microscopic scale. The system 100 comprises an optical lens 110 adapted to be operatively connected to an optical source, the optical lens 110 having an optically transparent surface 160 coated with transducers 140, a stimulus generator 120 adapted to be connected to the transducers 140 for generating a stimulus signal for stimulating the transducers 140, and an operating device 130 adapted to be connected to the stimulus generator 120 for controlling the stimulus signal. The transducers 140 can be sensors, actuators and/or transistors, electrodes, magnetic coils, and so on depending on the application. The optical lens 110 adapted in accordance with any of the embodiment of the present invention is interchangeably referred to herein as optical lens or functionalized optical lens.

The optical lens 110 has an optically transparent surface 160 coated with transducers 140 and is adapted to enable an optical communication between an optical source from one side of the optically transparent surface 160 and the transducers 140 and the sample(s) 170 from another side of the surface for enabling the optical source to conduct optical operations capturing both the transducers 140 and the sample(s) 170 simultaneously during a stimulation process. This is preferably conducted at a microscopic level. The sample 170 can either be a single biological sample on a surface, or can be a plurality of samples place on a surface under the optical source. In one embodiment of the invention, the optical operations comprise observing, visualizing, monitoring and/or recording images of the transducers 140 and the sample 170 during the stimulation process.

In one embodiment of the invention, the optical lens 110 is a microscope objective lens and the optical source is a microscope. In an embodiment of the invention, the optical lens 110 is a lens cap adapted to be mechanically coupled (permanently or temporarily or removably) to a microscope objective lens. When the optical lens 110 is a microscope objective lens or a lens cap adapted to be coupled to the microscope objective lens, the optical source comprises a microscope.

Figure 4:
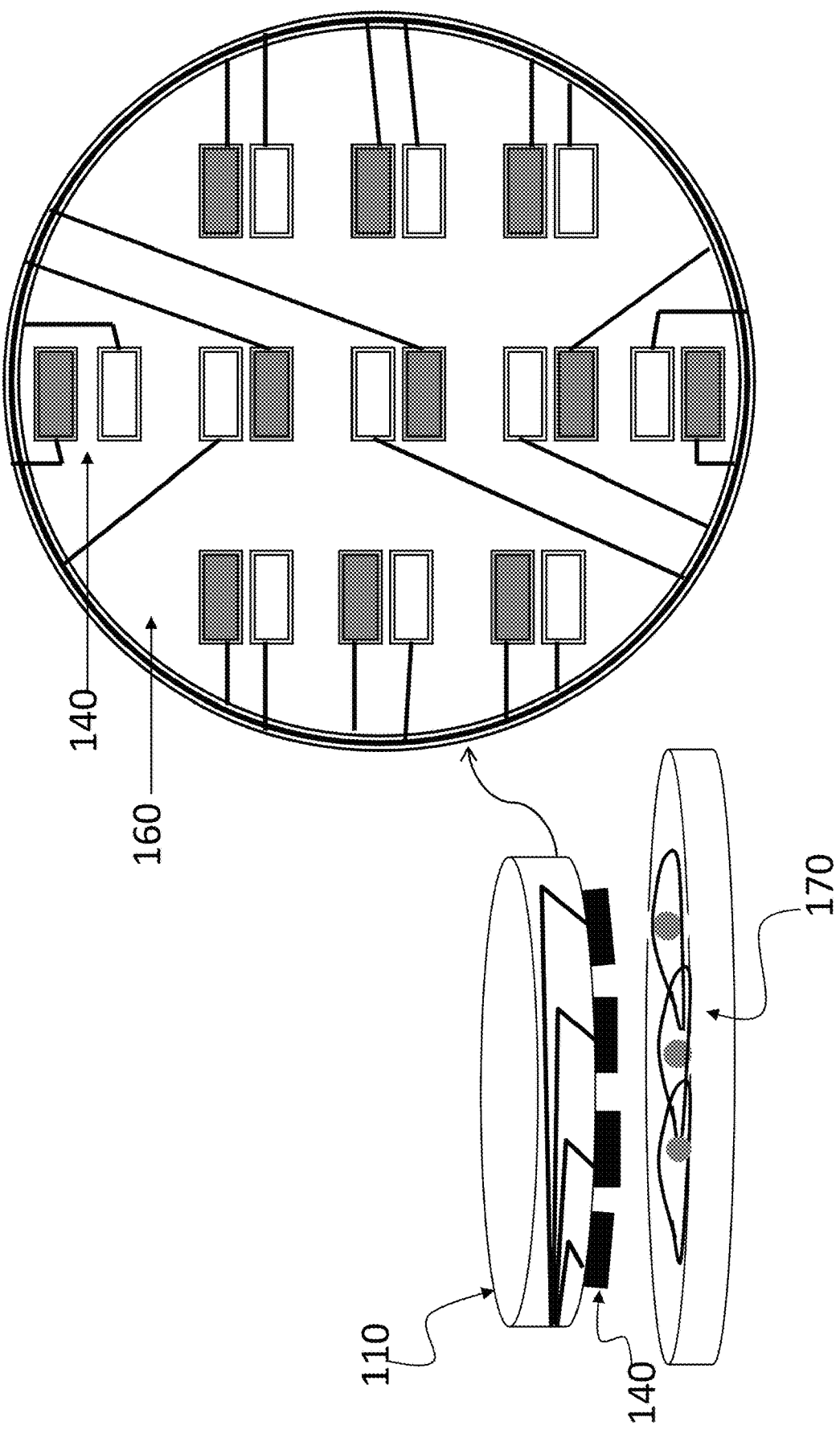
FIG. 4 illustrates an electrode array in accordance with an embodiment of the present invention.

In an embodiment of the invention, the transducers 140 comprise electrodes for applying an electrical stimulus to the samples 170 and, optionally, for sensing the electric stimulus response. The electrodes can be in the form of an electrode array, as depicted in FIG. 4. In another embodiment of the invention, the transducers 140 comprise magnetic coils for applying a magnetic stimulus to the samples 170 and, optionally, for sensing the magnetic stimulus response. Sensing the response of the stimulus may not be a requirement for all applications. For example, a possible application of this invention is the electroporation of living cells which would require the stimulation of an electrical field in the cells using electrodes, without necessarily sensing the response to the electrical field. This embodiment can be seen in FIG. 5, wherein the transducers 140 are in the form of magnetic coils, on the surface 160 of the optical lens 110.

Figure 5:
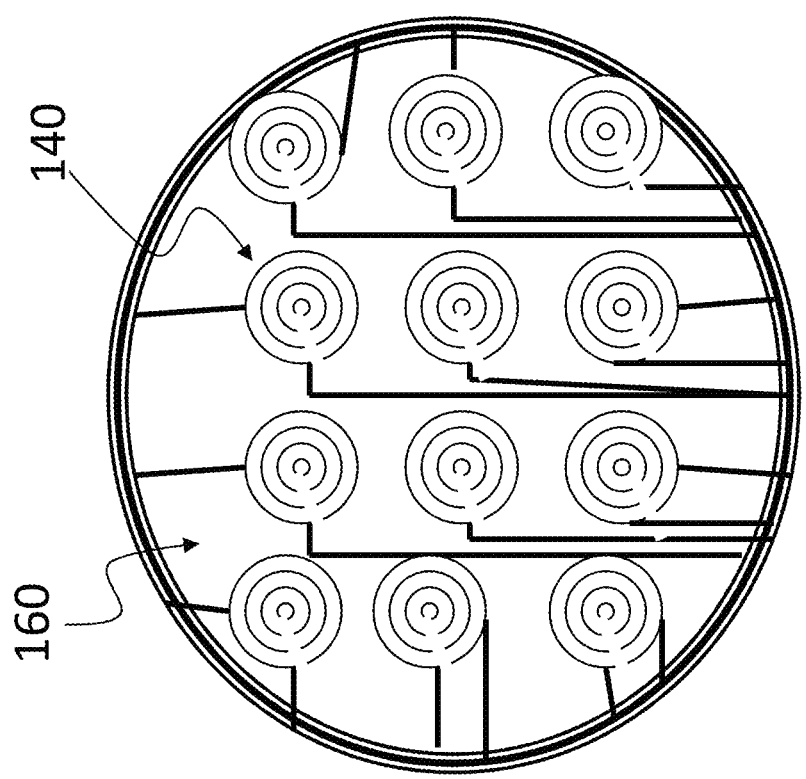
FIG. 5 illustrates an array of magnetic micro coils in accordance with an embodiment of the present invention.

The stimulus generator 120 is adapted to be connected to the transducers 140 for generating and transmitting a stimulus to the transducers 140. When the transducers 140 are electrodes, the stimulus generator 120 comprise an electrical pulse generator adapted to generate and transmit electrical stimulus signals to the transducers 140. When the transducers 140 are magnetic coils, as shown in FIG. 5, the stimulus generator 120 comprises a magnetic generator adapted to generate and transmit a magnetic field to the transducers 140. The transducers 140 are adapted to be deployed in such a manner to receive the stimulus, stimulate the stimulus in the samples 170 and, optionally, receive the stimulus response.

The operating device 130 is adapted to be connected to the stimulus generator 120 for controlling the stimulus, the controlling comprising determining the characteristics of stimulus. The operating device 130 comprises an interface system and a microprocessor/microcontroller in a computer or embedded system adapted to be connected to the interface system for the generation of appropriate stimulus signals for stimulation (amplitude, shape, number of events, frequency, duration of events) or detect the stimulus response signal (for instance capacitive, charge and so on).

The interface system preferably comprises various circuitries for stimulation or recording purposes. In an embodiment of the invention, the interface system is adapted to generate visual signals of the image of the sample 170 and the electrodes for visualisation on a computer display.

In an embodiment of the invention, the operating device 130 comprises a user interface for enabling a user to control the stimulus, for example by specifying the stimulus characteristics desired including frequency, power, amplitude, shape, duration, number and so on. The various transducers 140 can be controlled all having the same stimulus, or alternatively having varying stimulus characteristics, so that the response from the samples 170 can be analysed and monitored. Allowing the samples 170 to be stimulated separately, with different stimulus characteristics (frequency, power, amplitude, duration and so on) can aid in monitoring and determining the optimal conditions in which the samples 170 will be the most responsive to electroporation. In an embodiment of the invention, the user interface comprises a display.

In an embodiment of the invention, the operating device 130 is adapted to be connected to the transducers 140 for receiving the stimulus response from the transducers 140, determining the characteristics of the response and communicating these characteristics to the user through the user interface. The characteristics of the stimulus response can for instance be the capacitance, charge and so on.

In an embodiment of the invention, the operating device 130 is adapted to be connected to the optical source, such as the microscope, for receiving visual images captured during the stimulation process including images of the transducers 140 as they are positioned with respect to the samples 170 under the microscope. The operating device 130 is adapted to display these images on the display, preferably along with the characteristics of the stimulus response received for each one of the transducers 140.

Figure 3:
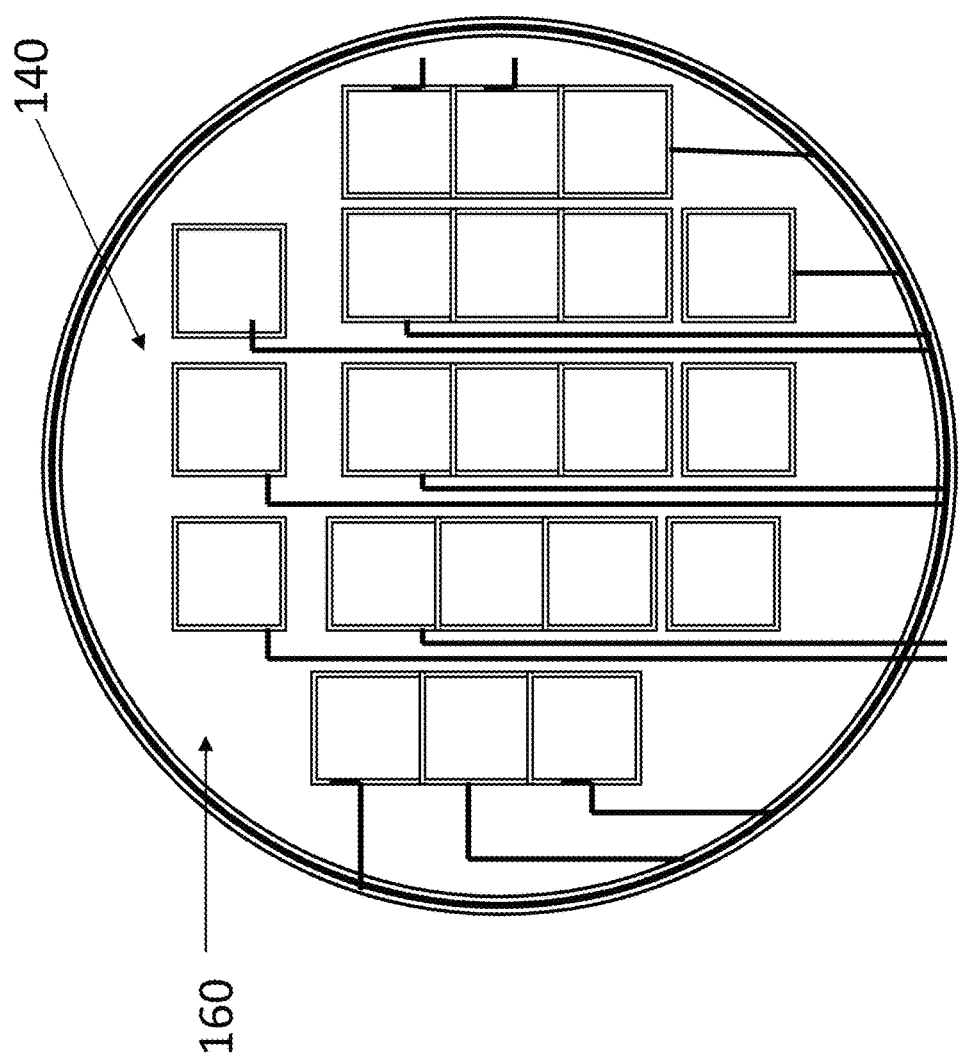
FIG. 3 illustrates a transducers array in accordance with an embodiment of the present invention.
Figure 6:
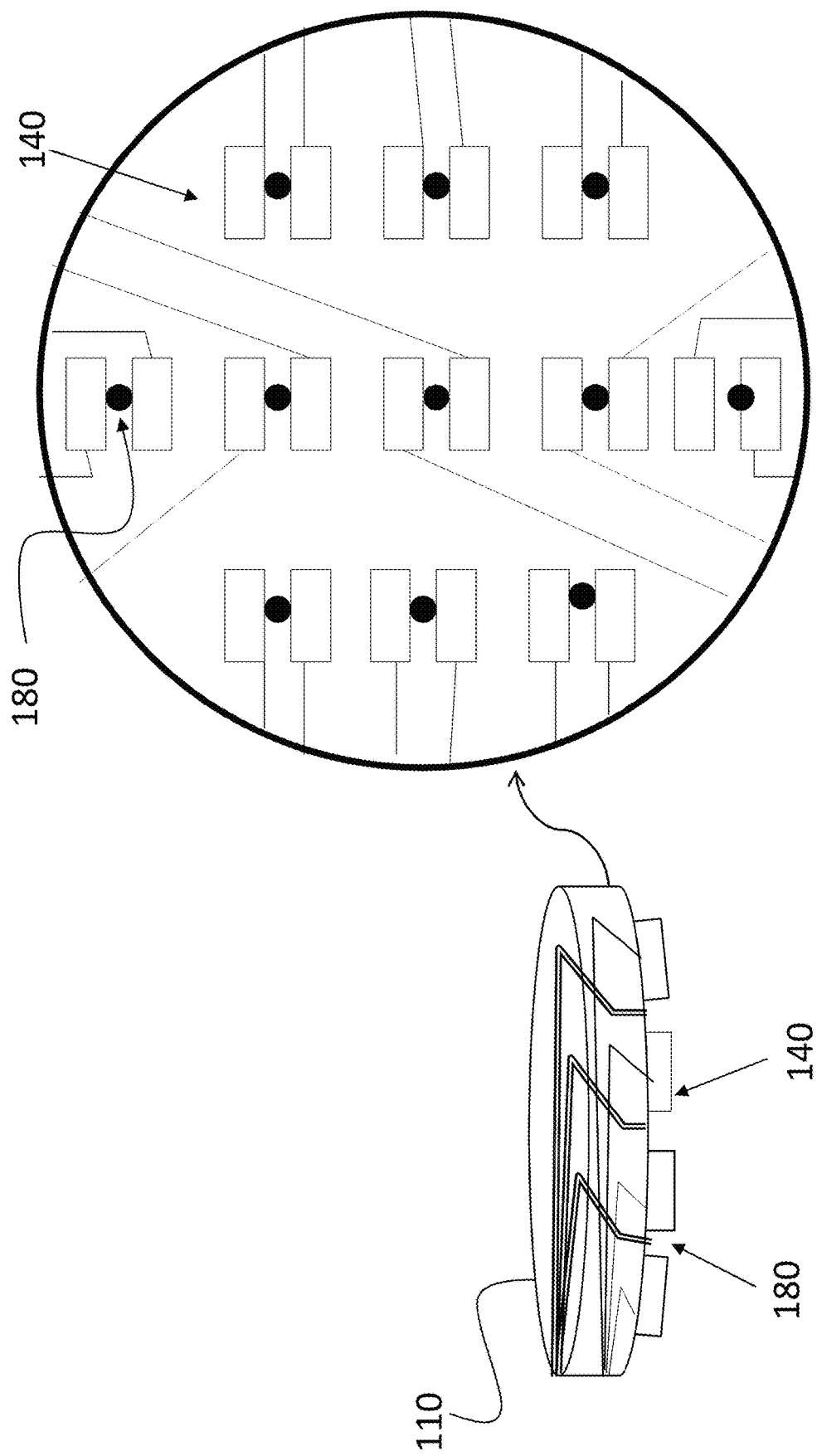
FIG. 6 illustrates microfluidic structures in accordance with an embodiment of the present invention.

In an embodiment of the invention, the system 100 is adapted for the electroporation of living cells using an electrical stimulus. According to this embodiment, the optical lens 110 has an optically transparent surface 160 with a microelectrodes array 140 printed/coated thereon, as shown in FIGS. 3, 4 and 6. Various possible configurations of electrode arrays are depicted in these foregoing figures. The microelectrodes array 140 is adapted to be electrically connected to the stimulus generator 120 which is a pulse generator in this case for receiving and applying electrical pulses for performing electroporation of living cells.

The connection between the microelectrodes array 140 and the pulse generator 120 is preferably a wire connection connecting each group of electrodes of the array to the pulse generator for control and multiplexing purposes. Each group of electrodes comprises one or more electrodes. Each group of electrodes (which can be one or more electrodes) can therefore be controlled individually and separately from the other electrodes of the array. This allows for stimulating the different groups of electrodes independently, which in turn allows for groups of samples 170 to be stimulated simultaneously with electrical fields having different electrical characteristics.

In an embodiment of the invention, the microelectrodes array 140 is produced on the transparent optical surface 170 using a sputtering deposition technique. Sputtering deposition provides better uniformity and adhesion of MEA 140 on the surface of the optical lens 110. The optimum thickness of the coated MEA 140 is within the range of 20-200 nm. The required thickness of the coated microelectrodes is obtained by modifying the parameters involved during the deposition technique used. For example when sputtering deposition technique is used, some parameters such as working pressure (mTorr), DC power (W), and the temperature of the substrate (° C.), are optimized for obtaining the required thickness of the coated material. Other coating processes can also be used, such as, chemical or physical vapour deposition (CVD or PVD).

For an efficient electroporation process of living cells, the size of a microelectrode should be similar to the size of a cell (around 20-30 micrometres), so that the living cells can be positioned near the edges of the microelectrodes. The distance between the cells and the microelectrodes can be adjusted, for example using the z-axis manipulator of the microscope objective. Each cell is being allocated two microelectrodes, one acting as a cathode and the other one as anode. This can be seen in FIGS. 4 and 6.

The Microelectrodes array (MEA) 140 can be made from any suitable metallic conductive material such as gold, or preferably from any suitable transparent conducting films, such as conductive polymers, metal grids, graphenes and, in particular, transparent conductive oxides (TCOs) such as Indium Tin Oxide (ITO). Preferably, the MEAs 140 of the present invention are made from ITO material due to its enhanced properties in terms of optical transparency and electrical conductivity. Optically transparent MEAs are preferably used so that the microscope objective is able to directly observe and control the electroporation process of the cells, especially the capability to also select the appropriate cell or cells to be transfected.

The electroporation process using the system of the present invention can be performed on more than 60,000 samples in few seconds. The microscope objective of the present invention offers new prospects for understanding the biophysical complexity of cell reprogramming as well as cell behaviours in a precisely controllable electrical field using a high throughput and rapid electroporation system.

In an embodiment of the invention, the microelectrodes are divided into pairs where each electrode pair comprises an anode and a corresponding cathode. In an embodiment of the invention, the electrodes 140 have a lateral arrangement where the anodes and cathodes are coated on the optically transparent surface 160 in pairs along a horizontal plan. According to this embodiment, during the stimulation process, the optically transparent surface 160 is positioned in proximity of the sample 170 and in such a manner that the sample 170 for stimulation is positioned intermediary the anode and the cathode along the horizontal plane. Although not shown in the Figures, when the sample 170 comprises one or more living cells for electroporation, each living cell is positioned intermediary an anode and a corresponding cathode forming the same electrode pair along the horizontal plan such that the electrical charges travel laterally between the anode and the corresponding cathode with the living cell positioned in between along the horizontal plane.

In another embodiment of the invention, there is provided a recipient adapted to carry the sample during the stimulation process, where the recipient has a surface coated with stimulus receivers (for example cathodes). According to this embodiment, the electrodes are arranged according to a vertical arrangement where the anodes are coated on the optically transparent surface 160 of the optical lens 110 and the cathodes are coated on the recipient surface carrying the sample 170 such that when the optical lens 110 is placed above and in proximity of the recipient along a vertical plan during the stimulation process, the electrical field travels vertically along the vertical plane between the anodes and the cathodes with the one or more living cells positioned in between.

The pulse generator 120 is adapted to be connected to the operating device 130 for receiving a control signal comprising the characteristics of the electrical pulses to be generated by the pulse generator 120. The signal characteristics comprise amplitude, frequency, form and number of pulses.

In an embodiment of the invention, the pulse generator 120 is adapted to generate different stimulus signals with different signal characteristics simultaneously. When the microelectrodes array 140 comprise one or more groups of electrodes multiplexed and connected independently to the pulse generator 120, this enables the pulse generator 120 to stimulate independently and simultaneously with each group of electrodes using different electrical conditions.

When each group of electrodes comprises a single electrode, this allows for each electrode of the array to be operated separately from the others but still simultaneously using corresponding electrical conditions. This allows for the simultaneous electroporation of the living cells using different electrical conditions. The simultaneous electroporation is time efficient for determining the optimal electrical conditions for transfecting the living cells.

The operating device 130 is adapted to enable the selection of one or more electrodes in the array for stimulation simultaneously or in alternation. Each electrode of the array can therefore be mapped for the transfection of a corresponding living cell which can be activated either in alternation or simultaneously with other electrodes either according to the same electrical conditions or according to different electrical conditions. In order to enable the simultaneous excitation of different electrodes according to different electrical conditions, in an embodiment of the invention, the pulse generator 120 is adapted to generate and transmit to the microelectrodes array 140 a series of electrical pulses with different electrical conditions simultaneously.

In an embodiment of the invention, the operating device 130 is adapted to be connected to the optical source (such as the microscope) for receiving optical images (such as video images) of the transducers (such as the microelectrodes) as they are positioned with respect to the samples 170 (such as the living cells). The visualization of the transducers 140 with respect to the samples 170 allows a user to manipulate the positioning of the transducers 140 with respect to the samples 170 which is very useful in multiple applications. Also, this makes it possible to simultaneously visualize the samples 170 during the stimulation process and manipulate the physical locations of the transducers 140.

In an embodiment of the invention, the operating device 130 is adapted to display the captured images on the display along with the characteristics of the signal stimulus and/or the signal stimulus response received for each one of the transducers 140. In an embodiment of the invention, the operating device 130 is adapted to enable a user to dynamically change the characteristics of the signal stimulus. This can be done based on the stimulus response and/or based on the visual images of the stimulated samples 170 received and displayed by the operating device 130. Therefore this allows for real time assessment of the stimulus response from the samples 170, and also real time manipulation of the stimulus signals.

Figure 7:
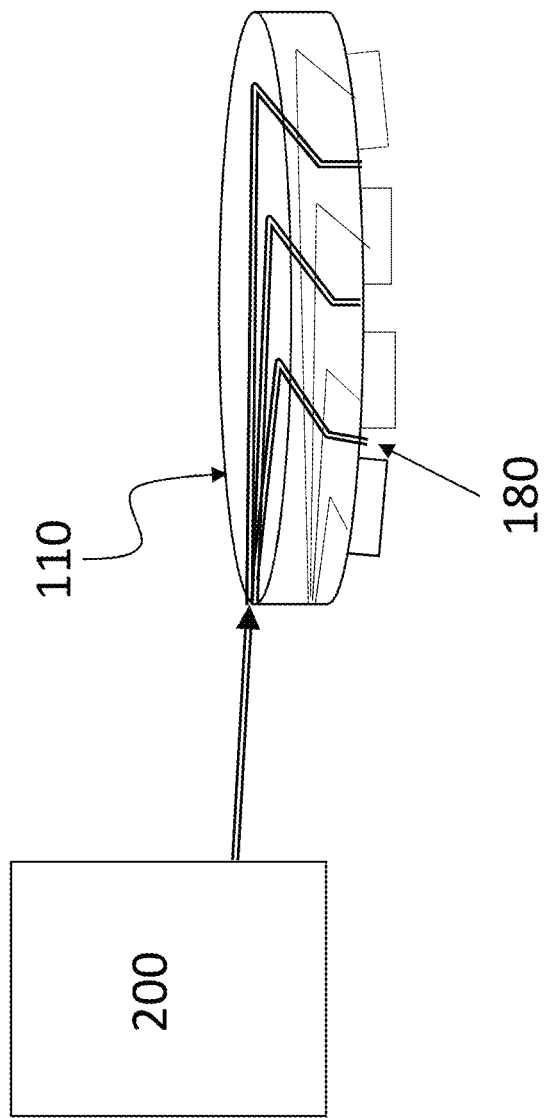
FIG. 7 illustrates a side view of a microfluidic structure in accordance with an embodiment of the present invention.

As can be seen in FIGS. 6 and 7, one embodiment of the invention provides that the optical lens 110 comprises microfluidic structures 180 for directing a fluid to the sample 170. The transducers 140 are coated on the optically transparent surface 160 with spaces formed between them through which fluid is directed from the microfluidic structures 180 and the fluid is directed onto the samples 170 or inserted inside the samples 170. The microfluidic structures 180 preferably comprises channels or chambers positioned above the transducers 140 (for example the electrodes array). The transducers 140 (such as the microelectrodes array) are designed to have through holes between them adapted to allow passage of the fluid in the direction of the sample 170.

In an embodiment of the invention, the microfluidics structures 180 are used along with a microelectrodes array 140, as seen on FIGS. 6 and 7, for the electroporation of living cells. In this case, the role of microfluidic structures 180 are to direct the required fluid samples 170 near the electrical field. For instance, there are several biological materials such as growth or differentiation factors that should be transfected inside the cells within the samples 170. The electrical field created using the microelectrodes 140 can create pores on the cells and fluid samples 170 can be directly injected into the cells. As depicted in FIG. 7, a fluid source 200 can be connected to the microfluidic structures 180 for supplying the fluid through the optical lens 110 and within the channels and to the samples 170. In one embodiment the fluid sources 200 can be a syringe pump. Other fluid sources and pumps can also be used, as would be appropriate for the type of fluid to be delivered to the samples 170.

The role of microfluidic structures 180 can be extended for many other applications requiring microscale or nanoscale fluid samples near the stimulations (such as the electrical stimulations). The main purposes of using a microfluidic structures 180 in the present invention is for biological delivery purposes, which can be useful a variety of biological protocols such as electroporation, di-electrophoresis, electrophoresis and electrophysiological studies in-vitro.

However, the optical lens 110 of the present invention has many more applications and microfluidic structures 180 can be used to deliver the required samples 170 for those purposes. According to an embodiment of the invention, the microfluidic structures 180 are adapted for the injection of filler (kind of glue) inside a metal surface where the samples 170 are positioned under the microscope lens 110. The presence of a gap can be detected by scanning the surface of the sample 170 using the optical lens 110 when in operative communication with the optical source (such as the microscope) and injecting the fluid using microfluidic structures 180 for filling the gap.

In an embodiment of the invention, the microfluidic structures 180 are made from silicon-based organic polymer such as PolyDiMethylSiloxane (PDMS), due to its optical transparency and inert and non-toxic properties.

According to various possible embodiments of the invention, the electrodes can be used for capacitive, impedometric, voltammetry, ammoperometric and other purposes. The operating device 130 can be adapted according to the specific applications.

In an embodiment of the invention, the optical lens 110 is a microscope objective lens having an optically transparent surface 160 coated with transducers (such as a microelectrodes array) 140.

In another embodiment of the invention, the optical lens 110 is a microscope objective cap having an optically transparent surface 160 coated with transducers (such as microelectrodes array) 140, where the cap is adapted to be mechanically coupled to the microscope objective. The microscope objective cap has suitable shape and dimensions adapted to be coupled to the microscope objective to be used during the stimulation process (such as electroporation). The cap can be manufactured in various structures and dimensions adapted for use with various models and dimensions of microscope objectives.

The optically transparent surface 160 of the optical lens 110 is made of optically transmissive material such as glass, plastic or silicon for example adapted to allow the passage of light in order to enable optical operations of the samples 170 during the stimulation process.

Among the achievements of the present invention is to integrate transducers (such as electrodes) 140 to a microscope objective lens, directly by coating the transducers (such as a microelectrode array) 140 on the microscope objective lens or, indirectly, through a suitable cap adapted to be coupled to the microscope objective lens, in such a manner to enable controlling the stimulation (such as the actuation and/or sensing process) of the samples 170 under the microscope (such as an electroporation process of living cells placed under the microscope) all in conducting real time optical operations in connection with the transducers 140 and the samples 170 during the sensing/actuation process (such as a visual monitoring and/or recording the transducers 140 and living cells during the electroporation process). The coupling of the cap to the microscope can be done permanently, temporarily and/or removably).

In an embodiment of the invention, the optical lens 110 is adapted to be moveable along the three dimensions in such a manner to enable a dynamic movability/positioning of the transducers 140 with respect to the samples 170. In this respect, the microscope objective itself, the cap, microscope head, the stage on which the samples 170 are placed, and/or any other component of the microscope or of the device on which the samples 170 are placed is adapted to be movable in order to enable a dynamic positioning of the transducers 140 with respect to the samples 170 including proximity from a three dimensional perspective. The order of proximity can range from centimetres to micrometres.

When the application is the electroporation of living cells, the position of the optical lens 110 carrying the microelectrodes array 140 would be movable with respect to the living cells in such a manner to allow the positioning of any desired microelectrodes 140 (among the other microelectrodes in the array) in a desired position with respect to the living cell (for example the positioning of the electrode directly above the culture cell). In general, in the electroporation process, the desired distance between the electrodes and the cells should be as close as 20-30 micrometres.

In an embodiment of the invention, the operating device 130 is adapted to be connected to the optical source (such as the microscope) for automatically controlling the movement of the optical lens 110 according to input instructions by a user, and the optical source is adapted to receive the instructions and automatically actuate movement of the optical lens 110 in accordance with the instructions received. The actuation of the movement of the optical lens 110 can be conducted indirectly, through the movement of another component coupled to the optical lens 110. For example, the operating device 130 can be adapted to actuate the movement of an adjustment mechanism associated with the optical source which would have as effect changing the positioning of the optical lens 110 with respect to the sample 170. When the optical source is a microscope, this can be the adjustment mechanism of the microscope.

Many changes, modifications, variations and other uses and applications of the subject invention will become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. An optical lens having an optically transparent surface integrated with transducers or through a cap coupled to the optical lens for electroporation of one or more living cells using an electrical stimulus, the optical lens comprising:
   a microfluidics structure comprising a plurality of channels integrated on the optical lens and positioned above the transducers, for directing a fluid within a sample for biological delivery purposes,
      wherein the optical lens enables an optical communication between an optical source from one side of the optically transparent surface and the transducers and the sample from another side of the optically transparent surface for enabling the optical source to conduct optical operations capturing both the transducers and the sample simultaneously during a stimulation process,
      wherein the optical lens is a microscope objective lens, the optical source is a microscope and the optical operations comprise observing, monitoring or recording images of the transducers and the sample during the stimulation process.

2. The optical lens of claim 1, wherein the optical lens is a lens cap adapted to be mechanically coupled to the microscope objective lens.

3. The optical lens of claim 1, wherein the sample and the transducers have a microscopic scale.

4. The optical lens of claim 1, wherein the optically transparent surface is made of glass, silicon or plastic, to allow passage of light in order to enable the optical operations.

5. The optical lens of claim 1, wherein the transducers comprise a microelectrode array and the stimulus signal is an electrical signal, wherein each group of electrodes are controlled individually and separately from other electrodes of the microelectrode array.

6. The optical lens of claim 5, wherein the sample comprises one or more living cells for electroporation through the stimulation of the electrical signal in the one or more living cells.

7. The optical lens of claim 1, wherein the transducers comprise magnetic coils on the surface of the optical lens and the stimulus signal is a magnetic field.

8. The optical lens of claim 1, wherein the transducers are microelectrodes, and the fluid is a drug for injection inside the one or more living cells during the stimulation process.

9. A system for electroporation of one or more living cells using an electrical stimulus, the system comprising:
an optical lens adapted to be operatively connected to an optical source,
wherein the optical lens comprises an optically transparent surface integrated with transducers and a microfluidics structure comprising a plurality of channels integrated on the optical lens and positioned above the transducers, for directing a fluid within a sample for biological delivery purposes;
a stimulus generator adapted to be connected to the transducers for generating a stimulus signal and for stimulating the stimulus signal in the sample using the transducers; and
an operating device is connected to an optical source for receiving and processing images captured through optical operations,
wherein the optical lens enables an optical communication between the optical source from one side of the optically transparent surface and the transducers and the sample from another side of the optically transparent surface for enabling the optical source to conduct optical operations capturing both the transducers and the sample simultaneously during a stimulation process,
wherein the optical lens is a microscope objective lens, the optical source is a microscope and the optical operations comprise observing, monitoring or recording images of the transducers and the sample during the stimulation process.

10. The system of claim 9, wherein:
the transducers comprise an array of microelectrodes and the stimulus signal is an electrical signal having signal characteristics;
the stimulus generator is an electrical pulse generator;
the operating device controls the pulse generator by specifying the signal characteristics of the electrical signal.

11. The system of claim 9, wherein the operating device is adapted to be connected to the optical source for receiving and processing images captured through the optical operations.

12. The system of claim 11, wherein the optical lens is a microscope objective lens or a lens cap adapted to be mechanically coupled to a microscope objective lens, and wherein the optical source is a microscope.

13. The system of claim 12, wherein the operating device is connected to an adjustment mechanism of the microscope for position adjustment of the optical lens with respect to the sample.

14. The system of claim 13, wherein the position adjustment is three dimensional to enable dynamic positioning of the transducers with respect to the sample, and is in the scale of centimetres to micrometres.

15. The optical lens of claim 10, wherein the sample comprises one or more living cells for electroporation through the stimulation of the electrical signal in the one or more living cells.

16. A method of manufacturing a stimulation device for use with an optical source for the electroporation of one or more living cells using an electrical stimulus, the method comprising:
integrating transducers on an optically transparent surface of an optical lens, or through a cap coupled to the optical lens;
generating a stimulus signal using a stimulus generator;
stimulating the stimulus signal in a sample using the transducers;
controlling the stimulus signal using an operating device adapted to be connected to the stimulus generator;
wherein the optical lens is adapted to enable an optical communication between the optical source from one side of the optically transparent surface and the transducers and the sample from another side of the optically transparent surface for enabling the optical source to conduct optical operations capturing both the transducers and the sample simultaneously during a stimulation process, and
wherein the optical lens comprises a microfluidics structure comprising a plurality of channels integrated on the optical lens and positioned above the transducers, for directing a fluid within the sample for biological delivery purposes, and the operating device is connected to the optical source for receiving and processing images captured through the optical operations,
wherein the optical lens is a microscope objective lens, the optical source is a microscope and the optical operations comprise observing, monitoring or recording images of the transducers and the sample during the stimulation process.

17. The method of manufacturing of claim 16, wherein the transducers are microelectrodes, the optical lens is a cap coupled to a microscope objective lens.

* * * * *